United States Patent

Hissung

[11] Patent Number: 5,186,709
[45] Date of Patent: Feb. 16, 1993

[54] CUVETTE ROTOR

[75] Inventor: Alfred R. Hissung, Marburg, Fed. Rep. of Germany

[73] Assignee: Behringwerke Aktiengesellschaft, Marburg, Fed. Rep. of Germany

[21] Appl. No.: 603,550

[22] Filed: Oct. 26, 1990

[30] Foreign Application Priority Data

Nov. 11, 1989 [DE] Fed. Rep. of Germany ....... 3937609

[51] Int. Cl.$^5$ .............................................. B04B 1/04
[52] U.S. Cl. ...................................... 494/43; 494/85; 422/64; 422/72
[58] Field of Search ...................... 494/16, 21, 31, 32, 494/33, 43, 45, 74, 79, 80, 85, 38, 41; 210/360.1, 369, 782; 422/72, 102, 63, 64; 356/246; 436/45, 177

[56] References Cited

U.S. PATENT DOCUMENTS

| 3,873,217 | 3/1975 | Anderson et al. | |
| 4,373,812 | 2/1983 | Stein | 356/246 |
| 4,580,897 | 4/1986 | Nelson | 356/246 |
| 4,902,479 | 2/1990 | Brikus | 422/72 |

FOREIGN PATENT DOCUMENTS 0052770 6/1982 European Pat. Off. .

OTHER PUBLICATIONS

European Search Report EP 90 12 1192 by Examiner C. A. Bindon completed on Oct. 24, 1991 at The Hague.

Primary Examiner—Harvey C. Hornsby
Assistant Examiner—Randall Edward Chin
Attorney, Agent, or Firm—Finnegan, Henderson, Farabow, Garrett and Dunner

[57] ABSTRACT

In the cuvette rotor (20) having circularly arranged and radially extending individual cuvettes (10) which are closed on all sides, each of the cuvettes (10) has two chambers (1, 2) which are separated from one another by a barrier (11). Each chamber (1, 2) is provided with an orifice (3, 4) for filling. Vessels (9) which are closed on all sides are arranged between the individual cuvettes (10), the bottom part (15) of each vessel having a barrier (13) which divides the vessel into two chambers (5, 6), and the upper part (14) being provided with an orifice (22) in the area of the chamber (5) arranged close to the axis of rotation and with a guard (12), which protrudes into the peripherally arranged chamber (6), in the area of the peripherally arranged chamber (6).

9 Claims, 1 Drawing Sheet

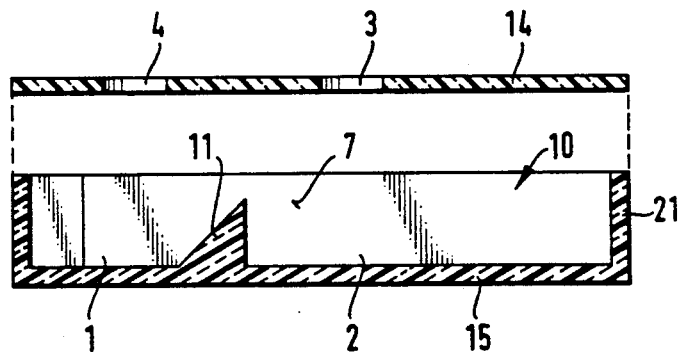
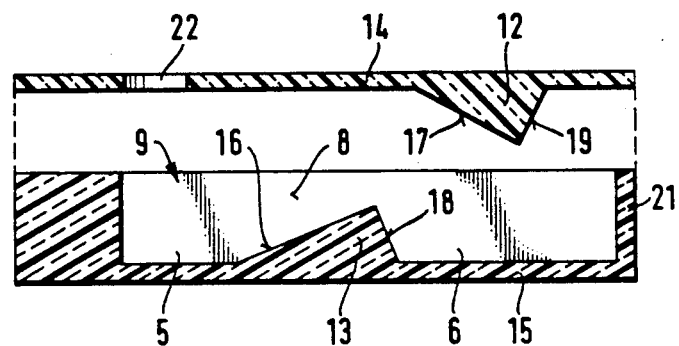
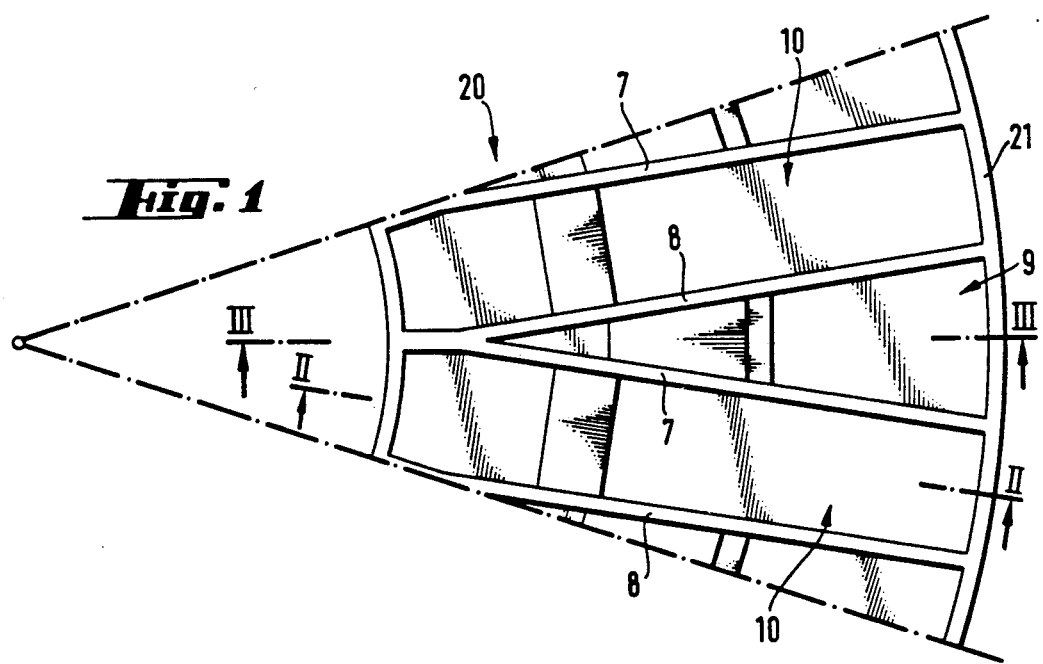

CUVETTE ROTOR

BACKGROUND

The invention relates to a cuvette rotor having individual, radially arranged cuvettes, as can be used in automatically operating analytical centrifuge systems for testing biological fluids, such as, for example, blood, blood plasma or blood serum.

The biological fluids are centrifuged before the analysis, if necessary, and mixed with specific reagents, as are, for example, required for PT, aPTT, fibrinogen and factor II to XII tests, in order to determine certain properties or substances contained herein, and the result of the reaction is recorded optically.

A cuvette rotor for analyses of this type is disclosed in European Patent Application 0,163,038. The individual, circularly arranged cuvettes extend radially and are closed on all sides. Each of them has two chambers which are separated from one another by a barrier and are provided with an orifice for filling. One chamber is charged with biological fluid and the other with specific reagent which mixes and reacts with the biological fluid as soon as the two liquids reach the peripherally arranged chamber due to the effect of the centrifugal forces. Optical measurement is carried out at right angles to the plane of the rotor through the peripherally arranged chamber with a fixed path length through the fluid to be analyzed.

SUMMARY OF THE INVENTION

The invention has the object of providing a cuvette rotor of the type mentioned on which further vessels for centrifuging samples are arranged, which vessels are independent of the individual cuvettes.

The object is achieved by a cuvette rotor wherein vessels which are closed on all sides are arranged between the individual cuvettes, the bottom part of each vessels having a barrier which divides the vessel into two chambers, and the upper part of which being provided with orifices in the area of the axially arranged chambers and with guards, which protrude into the peripherally arranged chambers, in the area of the peripherally arranged chambers.

The barriers can have rising and falling surfaces which extend in the radial direction of the rotor, the rising surfaces being less steep than the falling surfaces.

The advantage of the invention is primarily that additional separation vessels for centrifuging samples are arranged between the cuvettes in a space-saving way, thus considerably extending the possible applications of the cuvette rotor.

BRIEF DESCRIPTION OF THE DRAWING

In the following, the cuvette rotor is illustrated in more detail by means of drawings representing merely one embodiment, in which:

FIG. 1 shows a plan view of a section of the cuvette rotor without the upper part, FIG. 2 shows the section II—II of FIG. 1 with the upper part, and FIG. 3 shows the section III—III of FIG. 1 with the upper part.

DESCRIPTION OF THE PREFERRED EMBODIMENT(S)

The cuvette rotor (20) comprises cuvettes (10) which are closed on all sides and are delimited by side walls (7, 8), an upper part (14), a bottom part (15) and a front wall (21). The individual cuvettes (10) have chambers (1) and (2) which are separated from one other by a barrier (11). The barrier (11) is arranged on the bottom part (15). The barrier (11) is designed in such a way that, at the required volume of the chamber and with the rotor stationary, there can be no overflow into the adjacent chamber. The upper part (14) is provided with orifices (3 and 4) through which the inside of the chambers (1 and 2) can be reached.

The interspaces between the individual cuvettes (10) are designed as closed vessels (9) for centrifuging samples The vessels (9) are delimited by the side walls (7 and 8), the upper part (14), the bottom part (15) and the front wall (21). The vessels (9) are divided into the chambers (5 and 6) by barriers (13), which are arranged on the bottom part (15). The inside of the vessels can be reached via orifices (22) which are arranged in the upper part, namely above the chamber (5) close to the axis of rotation. Guards (12) extending from the upper part (14) protrude into the peripherally arranged chambers (6). The barriers (13) and the guards (12) are delimited at the sides by the walls (7 and 8) and have rising and falling plane or curved surfaces (16, 17, 18 and 19) which extend in the radial direction of the rotor (20). The rising surfaces (16 and 17) are less steep than the falling surfaces (18 and 19).

During centrifuging, the solid constituents present in the sample move radially in the direction of the front wall (21) of the vessel (9). Once centrifuging is completed and before the rotational motion of the cuvette rotor is braked, all solid constituents of the sample are in the peripheral chamber (6), namely between the front wall (21) and the guard (12) which is attached to the upper part (14), i.e. the interface between the solid constituents and the liquid is vertically behind the guard (12) in the peripheral chamber (6). During braking the rotational motion of the guard (12) ensures that the solid constituents remain in the peripheral chamber (6) behind the barrier (13). Part of the liquid flows without solid constituents, back over the barrier (13) into the chamber (5) close to the axis where it can then be removed through the orifice (22) in the upper part (14) with the aid of a syringe or pipette tip and, if desired, transferred into the cuvette (10).

I claim:

1. A cuvette rotor, comprising:
   a plurality of alternating cuvettes and vessels angularly disposed in a circle about a central axis,
   each cuvette for mixing a biological fluid with a reagent during rotation about the central axis,
   each vessel for centrifuging samples during rotation about the central axis,
   a cuvette barrier dividing each cuvette into first and second radially spaced chambers,
   a vessel barrier dividing each vessel into first and second radially spaced chambers,
   adjacent cuvettes and vessels of the plurality of alternating cuvettes and vessels having common sidewalls,
   a top covering the alternating cuvettes and vessels,
   the top having a cuvette orifice aligned with each of the cuvette chambers,
   the top having a vessel orifice aligned with one of the vessel chambers, and
   a guard for each of the plurality of vessels disposed on the top and extending a predetermined distance into one of the two vessel chambers of each vessel for preventing centrifuged material from remixing within the vessel.

2. The cuvette rotor of claim 1, wherein:
the guard is aligned with the second chamber of each vessel.

3. The cuvette rotor of claim 1, wherein:
the cuvette barrier, the vessel barrier, and the guard in cross-section have radially extending surface rising and falling outwardly from the central axis, the rising surfaces being disposed closer to the central axis than the falling surfaces.

4. The cuvette rotor of claim 3, wherein:
the absolute value of the slope of the falling surfaces is greater than the absolute value of the slope of the rising surfaces.

5. A cuvette rotor, comprising:
a circular array of alternating cuvettes and vessels angularly disposed about a central axis,
each cuvette for mixing a biological fluid with a reagent during rotation about the central axis,
each vessel for centrifuging samples during rotation about the central axis,
each cuvette having a top and a bottom being closed on all sides,
each cuvette defining two cuvette chambers separated from one another by a cuvette barrier,
each cuvette barrier extending from the bottom of the cuvette to a predetermined distance below the top,
the top having a cuvette orifice aligned with each cuvette chamber,
each vessel having a top and a bottom being closed on all sides,
each vessel having two vessel chambers separated from one another by a vessel barrier,
the two vessel chambers including a first vessel chamber, and a second vessel chamber radially disposed outwardly from the first vessel chamber,
the vessel barrier extending from the bottom of the vessel to a predetermined spaced distance from the top,
the top having a vessel orifice aligned with one of the two vessel chambers of each vessel, and
the top having a guard extending from the top a predetermined distance toward and spaced from the bottom of one of the first and second vessel chambers for preventing centrifuged material from remixing within the vessel.

6. The cuvette rotor of claim 5, wherein:
the guard is aligned with the second vessel chamber of each vessel.

7. The cuvette rotor of claim 5, wherein:
the vessel orifice is aligned with the first vessel chamber of each vessel.

8. The cuvette rotor of claim 5, wherein:
each cuvette barrier, vessel barrier, and guard have radially extending surfaces that rise and fall outwardly from the central axis, the rising surfaces being disposed closer to the central axis than the falling surfaces.

9. The cuvette rotor of claim 8, wherein:
the absolute value of the slope of the falling surfaces is greater than the absolute value of the slope of the rising surfaces.

* * * * *

UNITED STATES PATENT AND TRADEMARK OFFICE
CERTIFICATE OF CORRECTION

PATENT NO.   :   5,186,709
DATED        :   February 16, 1993
INVENTOR(S)  :   Alfred Rene Hissung It is certified that error appears in the above-identified patent and that said Letters Patent is hereby corrected as shown below:

Claim 3, column 3, line 10, change "surface" to --surfaces--.

Signed and Sealed this

Fourteenth Day of December, 1993

Attest:

BRUCE LEHMAN

*Attesting Officer*     *Commissioner of Patents and Trademarks*